United States Patent [19]

Wollweber et al.

[11] Patent Number: 4,952,601
[45] Date of Patent: Aug. 28, 1990

[54] FUNGICIDAL 3-CYANO-4-PHENYL-PYRROLE DERIVATIVES

[75] Inventors: Detlef Wollweber, Wuppertal; Wilhelm Brandes, Leichlingen, both of Fed. Rep. of Germany

[73] Assignee: Bayer Aktiengesellschaft, Leverkusen, Fed. Rep. of Germany

[21] Appl. No.: 266,468

[22] Filed: Nov. 2, 1988

[30] Foreign Application Priority Data

Nov. 9, 1987 [DE] Fed. Rep. of Germany ....... 3737983

[51] Int. Cl.$^5$ .................. A01N 43/36; C07D 207/34; C07D 405/04
[52] U.S. Cl. .................................... 514/427; 514/422; 548/526; 548/561
[58] Field of Search ................ 548/561, 526; 514/422, 514/427

[56] References Cited

U.S. PATENT DOCUMENTS 3,590,051  6/1971  Gorman et al. .................. 260/326.9

FOREIGN PATENT DOCUMENTS 0206999  6/1986  European Pat. Off. .
0236272  9/1987  European Pat. Off. .
2927480  1/1980  Fed. Rep. of Germany .

*Primary Examiner*—Mark L. Berch
*Attorney, Agent, or Firm*—Sprung, Horn, Kramer & Woods

[57] ABSTRACT

Fungicidal 3-cyano-4-phenyl-pyrrole derivatives of the formula

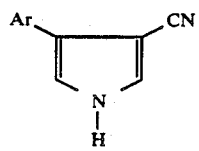

in which Ar stands for trisubstituted, tetrasubstituted or pentasubstituted phenyl.

8 Claims, No Drawings

FUNGICIDAL 3-CYANO-4-PHENYL-PYRROLE DERIVATIVES

The invention relates to new 3-cyano-4-phenyl-pyrrole derivatives, a process for their preparation, their use in pesticides, and new intermediates.

It has been disclosed that certain 3-cyano-4-phenyl-pyrroles, such as, for example, the compound 3-cyano-4-(2,3-dichlorophenyl)-pyrrole, possess fungicidal activity (cf., for example, EP No. 236,272).

However, the activity of these known compounds is not completely satisfactory in all fields of application, in particular at low application rates and concentrations.

New 3-cyano-4-phenyl-pyrrole derivatives of the general formula (I)

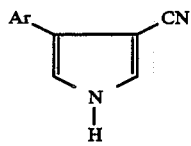

in which Ar stands for trisubstituted, tetrasubstituted or pentasubstituted phenyl, have been found.

Furthermore, it has been found that the new 3-cyano-4-phenyl-pyrrole derivatives of the general formula

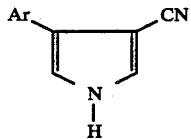

in which Ar stands for trisubstituted, tetrasubstituted or pentasubstituted phenyl, can be obtained when substituted cinnamonitriles of the formula (II)

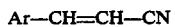

in which Ar has the abovementioned meaning, are reacted with sulphonylmethyl isocyanides of the formula (III)

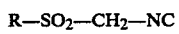

in which R stands for alkyl or for optionally substituted aryl, in the presence of a base and if appropriate in the presence of a diluent.

Finally, it has been found that the new 3-cyano-4-phenyl-pyrrole derivatives of the general formula (I) have a good action against pests.

Surprisingly, the 3-cyano-4-phenyl-pyrrole derivatives of the general formula (I) show a considerably better fungicidal activity than, for example, the 3-cyano-4-phenylpyrroles known from the prior art, such as, for example, the compound 3-cyano-4-(2,3-dichlorophenyl)-pyrrole, which are chemically similar compounds of a similar type of action.

Formula (I) provides a general definition of the 3-cyano-4-phenyl-pyrrole derivatives according to the invention. Preferred compounds of the formula (I) are those in which Ar stands for phenyl which is trisubstituted, tetrasubstituted or pentasubstituted by identical or different substituents, suitable substituents being halogen, in particular fluorine, chlorine or bromine, for alkyl, alkoxy or alkylthio, each straight-chain or branched and each having 1 to 4 carbon atoms, for halogenoalkyl, halogenoalkoxy or halogenoalkylthio, each straight-chain or branched and each having 1 to 4 carbon atoms and optionally 1 to 9 identical or different halogen atoms, for dioxyalkylene or halogenodioxyalkylene, each doubly linked and each having 1 or 2 carbon atoms and optionally 1 to 4 identical or different halogen atoms.

Particularly preferred compounds of the formula (I) are those in which Ar stands for phenyl which is trisubstituted, tetrasubstituted or pentasubstituted by identical or different substituents, particularly preferred substituents being fluorine, chlorine, bromine, methyl, methoxy, methylthio, trifluoromethyl, trifluoromethoxy, trifluoromethylthio, and dioxymethylene or difluorodioxymethylene, each doubly linked.

Very particularly preferred compounds of the formula (I) are those in which Ar stands for phenyl which is trisubstituted, tetrasubstituted or pentasubstituted by identical or different substituents, at least one of the substituents being fluorine and suitable other substituents being chlorine, bromine, methyl, methoxy, methylthio, trifluoromethyl, trifluoromethoxy, trifluoromethylthio or difluorodioxymethylene.

In addition to the compounds mentioned in the preparation examples, the following 3-cyano-4-phenyl-pyrrole derivatives of the general formula (I) may be mentioned individually:

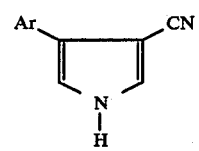

| Ar | Ar | Ar |
|---|---|---|

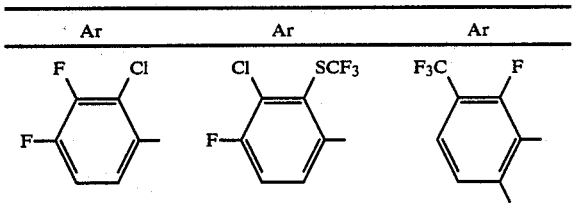

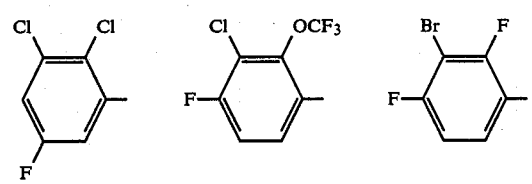

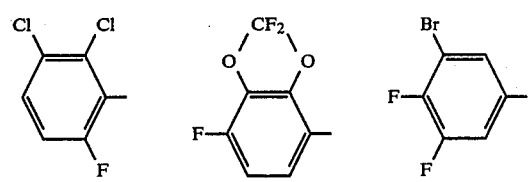

-continued

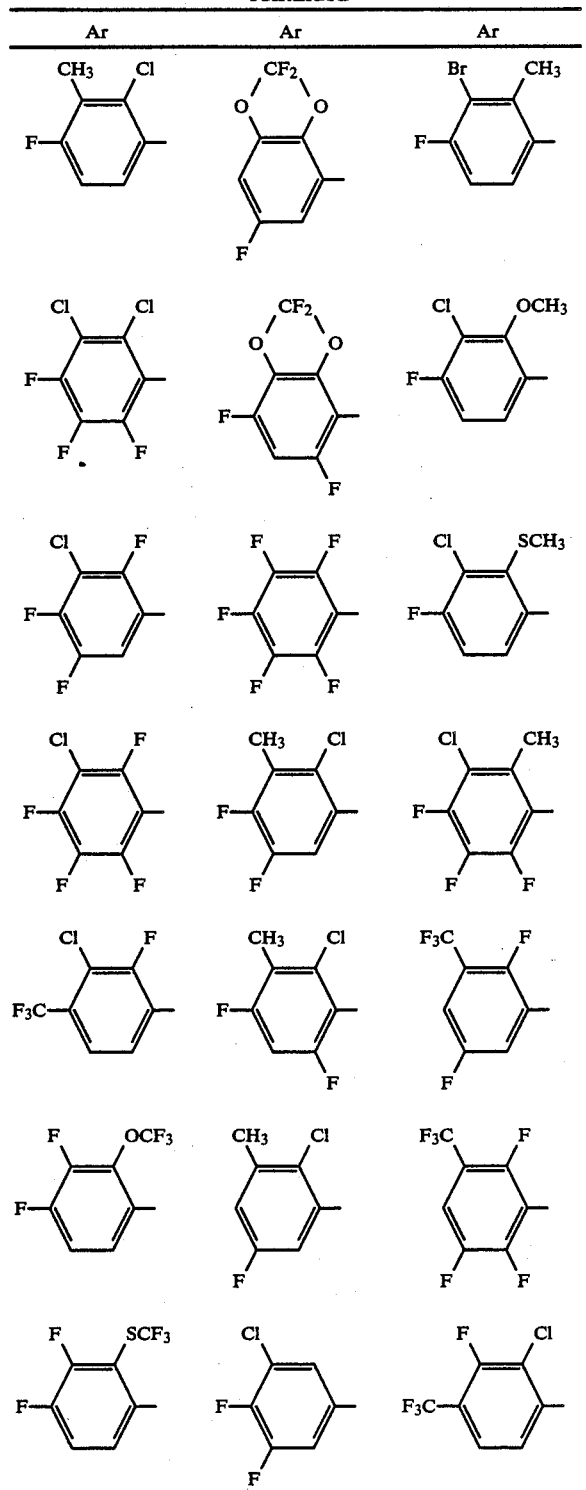

If, for example, 3,4-dichloro-2-fluorocinnamo-nitrile and p-toluenesulphonylmethyl isocyanide are used as the starting substances and sodium hydride is used as the base, the course of reaction of the process according to the invention may be represented by the following equation:

Formula (II) provides a general definition of the substituted cinnamonitriles required as starting substances for carrying out the process according to the invention. In this formula (II), Ar preferably stands for those radicals which have already been mentioned in connection with the description of the substances of the formula (I) according to the invention for this substituent.

The substituted cinnamonitriles of the formula (II) are new. However, they can be obtained in analogy with known processes (cf., for example, DE-OS (German Published Specification) No. 2,927,480), for example when (a) substituted anilines of the formula (IV)

$$Ar-NH_2 \qquad (IV)$$

in which Ar has the abovementioned meaning, are, initially in a first step, reacted with acrylonitrile under the customary diazotization conditions, for example in the presence of sodium nitrite and hydrochloric acid and in the presence of a suitable metal salt catalyst, such as, for example, copper(II) chloride or copper(II) oxide, and if appropriate in the presence of a suitable diluent, such as, for example, acetone or water, at temperatures between $-20°$ C. and $50°$ C. ("Meerwein arylation"; also cf. in this context Organic Reactions 11, 189 [1960]; Organic Reactions 24, 225 [1976] or C. Ferri "Reaktionen der organischen Synthese"[Reactions in Organic Synthesis]p. 319, Thieme Verlag Stuttgart (1978)), and in a 2nd step, the resulting substituted α-chloro-β-phenyl-propionitriles of the formula (V)

$$Ar-CH_2-\overset{Cl}{\underset{|}{CH}}-CN \qquad (V)$$

in which Ar has the abovementioned meaning, are dehydrohalogenated at temperatures between $0°$ C. and $50°$ C. with bases, such as, for example, triethylamine or diazabicycloundecene, in a customary manner and if appropriate in the presence of a diluent, such as, for example, tetrahydrofuran (also cf. the preparation examples) or, alternatively, (b) substituted benzaldehydes of the formula (VI)

(VI)

in which Ar has the abovementioned meaning, are subjected to a condensation reaction at temperatures between 50° C. and 120° C. together with cyanoacetic acid of the formula (VII)

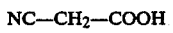

NC—CH₂—COOH                             (VII)

in a customary manner and in the presence of a base, such as, for example, piperidine or pyridine, and if appropriate in the presence of a suitable diluent, such as, for example, pyridine, and decarboxylation is simultaneously carried out (cf., for example, "Organikum" p. 571/572; 15th edition; VEB Deutscher Verlag der Wissenschaften Berlin 1981, and also preparation examples).

Some of the substituted anilines of the formula (IV) are known (cf., for example, J. org. Chem. 39, 1758–1761 [1974]; J. med. Chem. 12, 195–196 [1969] or U.S. Pat. No. 3,900,519).

New substituted anilines are for example those of the formula (IVa)

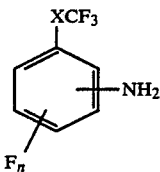

(IVa)

in which
X stands for oxygen or sulphur and
n stands for 2, are the subject of German Patent Application No. P 3 737 985 dated Nov. 9, 1987, corresponding to U.S. application Ser. No. 264,462 filed 10-28-88, now pending.

A generally applicable process for the preparation of compounds of the formula (IVa)

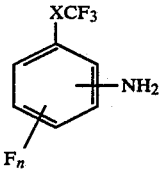

(IVa)

in which
X stands for oxygen or sulphur and
n stands for 2, is characterized in that compound-s of the formula (VIII)

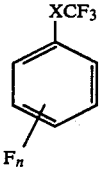

(VIII)

in which X and n have the meaning given for formula (IVa), are subjected to a nitration reaction, and the nitro compounds thus obtained are reduced.

The trifluoromethoxy- and trifluoromethylthiobenzenes which contain fluorine and which are to be employed in this process are known.

Nitrating can be carried out using customary nitrating agents, for example mixtures of nitric acid and sulphuric acid. In this reaction, the temperature can, for example, be in the range from 0° to 80° C., preferably, it is between 20° and 50° C. The nitrating agent can, for example, be employed in amounts such that, in the reaction mixture, 0.8 to 1.5 moles of nitrating agent are formed per mole of starting compound. Preferably, the amounts are chosen such that 1 to 1.1 moles of nitrating agent are formed per mole of starting compound. If appropriate, nitrating can be carried out in the presence of an inert organic solvent. A suitable solvent is, for example, dichloromethane.

The subsequent reduction can be carried out chemically, i.e., for example, using metals or metal salts which have a reducing action. Suitable metals or metal salts are, for example, iron, zinc, tin, tin(II) chloride and titanium(III) chloride. Reducing agents of this type are preferably employed in the stoichiometrically required amount. In a reduction of this type, the nitro compounds can be employed in the state in which they are obtained in the nitrating process or in which they are isolated afterwards. The reduction can also be carried out catalytically with hydrogen, it being possible, for example, to employ catalysts containing, or consisting of, metals. Suitable metals are, for example, those of subgroup VIII of the Periodic Table of the Elements, in particular palladium, platinum and nickel. The metals can be present in the elementary form or in the form of compounds, and also in particularly activated forms, for example, in the form of Raney metals or as metal or metal compound coated to support materials. Raney nickel, palladium-on-charcoal and aluminum oxide are preferred.

The catalytic reduction is preferably carried out in the presence of a solvent. Suitable solvents are, for example, alcohols and ethers, such as methanol, ethanol and tetrahydrofuran. The catalytic reduction can, for example, be carried out at temperatures in the range 0° to 80° C. and, for example, at hydrogen pressures in the range 1 to 100 bar. Excess hydrogen is generally not critical.

In the catalytic reduction, it is preferred to use acid-free nitro compounds. If necessary, the latter are thus to be freed from acids, for example by washing with water or neutralization with a base.

Working up of the reaction mixture after the chemical reduction or the catalytic hydrogenation can, for example, be carried out such that initially any solid constituents are filtered off, and the filtrate is distilled, if appropriate, after having been washed with water. If a mixture of isomers is obtained as the reaction product, it can be separated by precision distillation.

Compounds of the formula (IVa) having the fluorine in the o- and p-position relative to the amino group can also be prepared by reacting- compounds of the formula (IX)

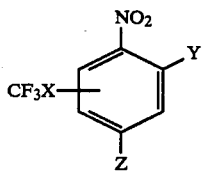

(IX)

in which
X stands for oxygen or sulphur and
Y and Z stand for chlorine,
with potassium fluoride in the presence of tetramethylenesulphone, in which reaction the chlorine present is replaced by fluorine, and by then carrying out a reduction, converting the nitro group to an amino group.

Compounds of the formula (IX) are known (cf. Houben-Weyl, Methoden der organischen Chemie [Methods in Organic Chemistry] E 4, p. 633 et seq.).

It is possible, for example, to employ 0.5 to 3 moles of potassium fluoride per equivalent of chlorine to be exchanged for fluorine in the compound of the formula (IX). This amount is preferably 1.2 to 1.5 moles. Tetramethylenesulphone acts as a solvent and is preferably employed at least in an amount such that the reaction mixture can be readily stirred. Relatively large amounts of solvent do not disturb the reaction.

Suitable temperatures for the reaction with potassium fluoride in tetramethylenesulphone are for example those in the range from 160° to 230° C. Preferred temperatures are those from 180° to 210° C. The reaction is preferably carried out in an environment which is as anhydrous as possible. This can for example be achieved by adding the compound of the formula (IX) carefully dried as the last component and by distilling off a small amount of tetramethylenesulphone together with any water present from the other components previously mixed together.

When the reaction is complete, solids present in the reaction mixture and, if desired, all or some of the tetramethylenesulphone can be removed.

Subsequent reduction of the nitro group to the amino group and working up of the resultant reaction mixture can be carried out in a manner as previously described in the generally applicable process for the preparation of the compounds of the formula (IVa).

It is also possible to prepare compounds of the formula (IVa) with X=oxygen by reacting compounds of the formula (X)

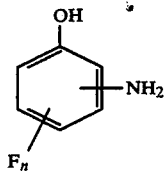

(X)

in which
n stands for 2, with carbon tetrachloride in the presence of hydrogen fluoride, the OH group being converted to a CF₃O group.

Compounds of the formula (X) are known (cf. French Patent No. 2,446,805).

It is possible to employ, for example, 1 to 10 moles of carbon tetrachloride and 5 to 30 moles of hydrogen fluoride per mole of the respective compound of the formula (X). Even a relatively large excess of carbon tetrachloride and hydrogen fluoride do not generally interfere. Suitable reaction temperatures, for example, are those in the range from 100° to 150° C. This process is preferably carried out under pressure, for example by releasing the resultant hydrogen chloride gas only above a certain pressure. This pressure can, for example, be at 18 to 60 bar. If desired, it is possible to include an additional inert gas, for example 1 to 20 bar nitrogen. It is advantageous to stir the mixture well during the reaction.

Working up of the reaction mixture can, for example, be carried out such that the reaction mixture is cooled to room temperature and the pressure is released, excess hydrogen fluoride and excess carbon tetrachloride are distilled off, for example at temperatures up to 80° C., the residue is poured onto ice water, the mixture is rendered alkaline with sodium hydroxide solution, and the organic phase is extracted with dichloromethane and subjected to precision distillation after drying.

Furthermore new trifluoromethylaminobenzenes containing fluorine and/or chlorine are those in which the trifluoromethyl group is in the 1-position, the amino group is
 (a) in the 2-position and two fluorine atoms are in the 5- and 6-positions, or one fluorine atom is in the 5-position and one chlorine atom in the 6-position, or
 (b) in the 3-position and two fluorine atoms are in the 2- and 6-positions, or one chlorine atom is in the 2-position and one fluorine atom is in the 6-position, or
 (c) in the 4-position and one fluorine atom is in the 2-position and, in addition, a further fluorine atom is in the 3- or 6-position, or two other fluorine atoms are in the 5- and 6-position or one other fluorine atom is in the 6-position and two chlorine atoms are in the 3- and 5-positions, or one chlorine atom is in the 3-position, or two chlorine atoms are in the 3- and 5-positions, or
 (d) in the 4-position and two fluorine atoms are in the 3- and 5-positions, or two chlorine atoms are in the 2- and 3-positions, or one fluorine atom is in the 3-position and one chlorine atom is in the 5-position.

These amines are the subject-matter of German Patent Application No. P 3 737 986 dated Nov. 9, 1987 corresponding to U.S. application Ser. No. 261,795, filed 10-24-88, now abn.

These compounds may be mentioned individually: 2-amino-5,6-difluoro-benzotrifluoride, 2-amino-5-fluoro-6-chloro-benzotrifluoride, 2,6-difluoro-3-amino-benzotrifluoride, 2-chloro-3-amino-6-fluoro-benzotrifluoride, 2,3-difluoro-4-amino-benzotrifluoride, 2,6-difluoro-4-amino-benzotrifluoride, 2,5,6-trifluoro-4-amino-benzotrifluoride, 2,6-difluoro-3,5-dichloro-4-amino-benzotrifluoride, 2-fluoro-3-chloro-4-amino-benzotrifluoride, 2-fluoro-3,5-dichloro-4-amino-benzotrifluoride, 3,5-difluoro-4-amino-benzotrifluoride, 2,3-dichloro-4-amino-benzotrifluoride and 3-fluoro-4-amino-5-chloro-benzotrifluoride.

A preferred process for the preparation of trifluoromethylaminobenzenes which contain fluorine and/or chlorine and in which the trifluoromethyl group is in the 1-position, the amino group
 (a) is in the 2-position and two fluorine atoms are in the 5- and 6-positions, or one fluorine atom is in the 5-position and one chlorine atom is in the 6-position, or (b) is in the 3-position and two fluorine atoms are in the 2- and 6-positions, or one chlorine atom is in the 2-position and one fluorine atom is in the 6-position, or (c) is in the 4-position and one fluorine atom is in the 2-position and in addition another fluorine atom is in the 3- or 6position, or two other fluorine atoms are in the 5- and 6-positions, or one other fluorine atoms is in the 6-position and two chlorine atoms are in the 3- and 5-positions, or one chlorine atom is in the 3-position, or two chlorine atoms are in the 3- and 5-positions or (d) is in the 4-position and two fluorine atoms are in the 3- and 5-positions, or two chlorine atoms are in the 2- and 3-positions, or one fluorine atom is in the 3-position and one chlorine atom is in the 5-position, is characterized in that corresponding trifluoromethylbenzenes containing fluorine and/or chlorine are nitrated and the resultant trifluoromethylnitrobenzenes containing fluorine and/or chlorine are reduced.

The trifluoromethylbenzenes which contain fluorine and/or chlorine but are free of amino groups and which are to be employed in this process are known (cf., for example, J. Chem. Soc. C, (8), 1547–9 (1971)).

The nitration can be carried out using customary nitrating agents, for example mixtures of nitric acid and sulphuric acid. In this reaction, the temperature can be, for example, in the range from 0° to 80° C., preferably it is at 20° to 50° C. For example, the nitrating agent can be employed in amounts such that, in the reaction mixture, 0.8 to 1.5 moles of nitrating substance are formed per mole of starting compound. Preferably, an amount of nitrating agent is employed such that 1 to 1.1 moles of nitrating substance are formed per mole of starting compound. If appropriate, the nitration can be carried out in the presence of an inert organic solvent. An example for a suitable solvent is dichloromethane.

The subsequent reduction can be carried out chemically, i.e., for example, using metals or metal salts having a reducing action. Suitable metals or metal salts are, for example, iron, zinc, tin, tin(II) chloride and titanium(III) chloride. Reducing agents of this type are preferably employed in the stoichiometrically required amount. In a reduction of this type, the nitro compounds can be employed, for example, in the form in which they are obtained in the nitration or in the purified form.

Alternatively, the reduction can be carried out catalytically, using hydrogen, it being possible, for example, to employ catalysts containing, or consisting of, metals. Suitable metals are, for example, those of subgroup VIII of the Periodic Table of the Elements, in particular palladium, platinum and nickel. The metals can be present in the elementary form or in the form of compounds, and also in particularly activated forms, for example in the form of Raney metals, or as metal or metal compounds coated onto support materials. Preferred catalysts are Raney nickel, palladium-on-charcoal and aluminum oxide.

The catalytic reduction is preferably carried out in the presence of a solvent. Suitable solvents are, for example, alcohols and ether, such as methanol, ethanol and tetrahydrofuran. The catalytic reduction can, for example, be carried out at temperatures in the range from 10° to 60° C. and, for example, at hydrogen pressures in the range 1 to 100 bar. Excess hydrogen is generally not critical.

It is preferred to use acid-free nitro compounds for the catalytic reduction. Thus, if necessary, they are to be freed from acids after they have been prepared, for example by washing with water or neutralization with a base.

Working up of the reaction mixture after the chemical reduction or the catalytic hydrogenation can, for example, be carried out such that, initially, any solid constituents are filtered off and the filtrate is distilled, if desired after having been washed with water. If a mixture of isomers is obtained as the reaction product, it can, if desired, be separated by precision distillation.

A variant of the previously described catalytic reduction is carried out in the presence of a base, for example, in the presence of hydroxides or carbonates of the alkali metals of the tertiary amines. Preferred compounds are tertiary amines such as triethylamine or pyridine. With each equivalent of base per mole of the nitro compound employed in the catalytic reduction, an additional equivalent of chlorine atoms can be split off the former during the catalytic reduction. Thus, it is possible, for example, to obtain aminobenzotrifluorides, free from chlorine and containing fluorine, from nitrobenzotrifluorides containing fluorine and chlorine.

Another process specifically for the preparation of trifluoromethylaminobenzenes which contain fluorine and/or chlorine and in which the trifluoromethyl group is in the 1-position, the amino group (a') is in the 2-position and two fluorine atoms are in the 5- and 6-positions, or one fluorine atom is in the 5-position and one chlorine atom is in the 6-position, or (b') is in the 4-position and one fluorine atom is in the 2-position, and, in addition, another fluorine atom is in the 3- or 6-position, or two other fluorine atoms are in the 5- and 6-positions, or one other fluorine atom is in the 6-position and two chlorine atoms are in the 3- and 5-positions, or one chlorine atom is in the 3-position, or two chlorine atoms are in the 3- and 5-positions, or (c') is in the 4-position and two fluorine atoms are in the 3- and 5-positions, or two chlorine atoms are in the 2- and 3-positions, or one fluorine atom is in the 3-position and one chlorine atom is in the 5-position, is characterized in that the corresponding 2- and/or 4-halogeno-trifluoromethylbenzenes containing fluorine and/or chlorine are reacted with ammonia, under increased pressure and in the presence of an organic solvent.

The 2- and/or 4-halogeno-trifluoromethylbenzenes to be employed in this process have been disclosed (cf. EP No. 34,402).

It is possible for the ammonia to be added in the liquid or gaseous form, for example, as a substance (gaseous or liquid) or as an aqueous solution. For example, it is possible to employ 1 to 10 moles of ammonia per mole of halogen atoms in the 2- and/or 4-position to be replaced by $NH_2$ groups. Preferably, this amount is 3 to 8 moles. In this conversion, suitable temperatures are, for example, those in the range from 80° to 160° C., preferably those in the range from 100° to 130° C. The conversion can be carried out under the inherent pressure of the ammonia formed at the reaction temperature in the sealed vessel, which pressure can, for example, be in the range from 10 to 20 bar. It is also possible to employ higher pressures, for example up to 100 bar.

Suitable solvents which can be employed in this reaction are inert or virtually inert organic solvents of a very wide range. Suitable solvents are, for example, alcohols, ethers, sulphones and aromatic hydrocarbons.

The desired reaction product can be obtained from the reaction mixture present after the reaction by, for example, initially cooling and releasing the pressure, then removing the solvent, and then carrying out a distillation, preferably under reduced pressure.

Most of the fluorobenzaldehydes of the formula (VI) furthermore required as precursors for the preparation of the new starting compounds of the formula (II) in variant (b) are known (cf., for example, Jap. Pat. 58-222 045=C.A. 100: 209 288k), likewise, the cyanoacetic acid of the formula (VII) is generally known (cf. Organikum "Organischchemisches Grundpraktikum", Berlin 1977, VEB Deutscher Verlag der Wissenschaften, page 573).

Formula (III) provides a general definition of the sulphonylmethylisocyanides required as starting substances for carrying out the process according to the invention. In this formula (III), $R^1$ preferably stands for methyl or for optionally monosubstituted phenyl, such as, for example, 4-methylphenyl, 4-chlorophenyl or phenyl.

The sulphonylmethylisocyanides of the formula (III) are known (cf., for example, Synthesis 1985, 400–402; Org. Syntheses 57, 102–106 [1977]; J. org. Chem. 42, 1153–1159 [1977]; Tetrahedron Lett. 1972, 2367–2368).

Suitable diluents for carrying out the process according to the invention are inert organic solvents. These include in particular aliphatic, alicyclic or aromatic hydrocarbons, optionally halogenated, such as, for example, benzine, benzene, toluene, xylene, chlorobenzene, petroleum ether, hexane, cyclohexane, dichloromethane, chloroform and carbon tetrachloride, or ethers, such as diethyl ether, dioxane, tetrahydrofuran, ethylene glycol dimethyl ether or ethylene glycol diethyl ether, or amides, such as dimethylformamide, dimethylacetamide, N-methylformanilide, N-methylpyrrolidone or hexamethylphosphoric triamide, or sulphoxides, such as dimethyl sulphoxide.

If appropriate, the process according to the invention can be carried out in a two-phase system, such as, for example, water/toluene or water/dichloromethane, if appropriate in the presence of a phase-transfer catalyst. Compounds which may be mentioned as examples for such catalysts are tetrabutylammonium iodide, tetrabutylammonium bromide, tributyl-methylphosphonium bromide, trimethyl-$C_{13}$/$C_{15}$-alkylammonium chloride, dibenzyl-dimethylammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride, trimethylbenzylammonium chloride.

The process according to the invention is preferably carried out in the presence of a suitable base. Suitable bases are all inorganic and organic bases customarily employed. The hydrides, hydroxides, amides, alcoholates, carbonates or hydrogen carbonates of alkali metals, such as, for example, sodium hydride, sodium amide, sodium hydroxide, sodium methylate, sodium ethylate, potassium t-butylate, sodium carbonate or sodium hydrogen carbonate, or tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are used.

When carrying out the process according to the invention, reaction temperatures may be varied within a relatively wide range. In general, the reaction is carried out at temperatures between $-30°$ C. and $+120°$ C., preferably at temperatures between $-20°$ C. and $+50°$ C.

For carrying out the process according to the invention, 1.0 to 2 moles, preferably 1.0 to 1.5 moles, of sulphonylmethylisocyanide of the formula (III) and 1.0 to 2.0 moles, preferably 1.0 to 1.5 moles, of base are generally employed per mole of substituted cinnamonitrile of the formula (II). In this process, it may be advantageous to carry out the reaction under a protective gas atmosphere, such as, for example, argon. The reaction is carried out, and working up and isolation of the reaction products are carried out by generally customary methods.

As an alternative to the preparation of the active compounds according to the invention with the aid of the preparation process according to the invention, various other preparation processes for the preparation of the active compounds according to the invention may be considered.

Thus, active compounds of the formula (I) according to the invention are likewise obtained when, for example, α-cyanocinnamic acid ester is reacted with p-toluene-sulphonylmethylisocyanide in the presence of bases and in the presence of copper(II) salts (cf. J6-1030-571 or J6-1200-984), or when α-substituted cinnamonitriles are cyclized with isocyanoacetic acid esters in the presence of sodium hydride, the resultant pyrrole-2-carboxylic acid esters are hydrolyzed with bases and then thermally decarboxylized (cf. JP No. 59/212 468), or when phenacylamine derivatives are reacted with suitably substituted acrylonitrile derivatives (cf. No. EP No. 174,910), or when 3-trifluoro-methyl-4-phenyl-pyrroles are reacted with ammonia at an elevated temperature and an elevated pressure (cf. No. EP No. 182,738), or when 3-cyano-4-phenyl-$\Delta^2$-pyrrolines are oxidized in the presence of copper(II) salts or iron(III) salts (cf. EP No. 183,217), or when α-cyanoacrylic acid derivatives are reacted with isocyanoacetic acid esters in the presence of a base, and the resultant $\Delta^2$-pyrroline-2-carboxylic acid derivatives are, in a second step, oxidatively decarboxylated in the presence of a base and in the presence of a metal salt catalyst cf. German Patent Application No. P 3,718,375 of June 2, 1987, corresponding to U.S. application Ser. No. 197,065, filed 5/19/88, now U.S. Pat. No. 4,912,229.

The active compounds according to the invention exhibit a strong action against pests and can be employed in practice for combating undesired noxious organisms. The active compounds are suitable for the use as plant protective agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus*. (conidia form: Drechslera, syn: Helminthosporium); Uromyces species, such as, for example, *Uromyces appendiculatus*; Puccinia species, such as, for example, *Puccinia recondita;* Tilletia species, such as, for example, *Tilletia caries;* Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botryis cinerea*; Septoria species, such as, for example, *Septoria nodorum*; Leptosphaeria species, such as, for example, *Leptosphaeria nodorum*; Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be employed with particularly good success in the combating of diseases in fruit and vegetable growing, such as, for example, against the causative organism of gray mold of beans *Botrytis cinerea*), or for the combating of rice diseases, such as, for example, against the causative organism of rice blast disease (*Pyricularia oryzae*).

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, and furthermore ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

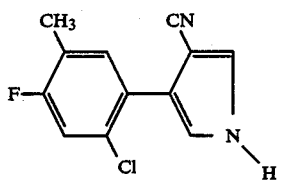

A solution of 6.0 g (0.0308 mol) of 3-(4-fluor-2-chloro-5-methyl-phenyl)-acrylonitrile and 7.8 g (0.0431 mol) of p-toluenesulphonylmethylisocyanide in 20 ml of a mixture of tetrahydrofuran/dimethyl sulphoxide (5:1) is added dropwise at −10° C. to −20° C. and with stirring to 1.3 g (0.0431 mol) of sodium hydride (80% strength in mineral oil) in 16 ml of tetrahydrofuran, under an argon protective gas atmosphere. When the addition is complete, the reaction mixture is allowed to warm to room temperature, water is added, the mixture is extracted several times with ethyl acetate, the combined ethyl acetate phases are washed with water, dried over sodium sulphate and concentrated in vacuo. The residue is purified by chromatography on silica gel (mobile phase: cyclohexane/ethyl acetate 5:1).

4.8 g (67% of theory) of 3-cyano-4-(4-fluoro-2-chloro-5-methyl-phenyl)-pyrrole of melting point 132° C.–133° C. is obtained.

In a corresponding manner and in accordance with the general instructions for the preparation, the following 3-cyano-4-phenyl-pyrrole derivatives of the general formula (I) can be obtained:

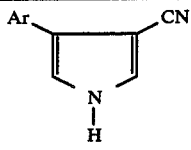

| Example No. | Ar | Melting point [°C.] |
|---|---|---|
| 2 | Cl, F, F (phenyl) | 184–185 |
| 3 | F₃C, Cl, Cl (phenyl) | 155–157 |
| 4 | Cl, F, F (phenyl) | 218–219 |
| 5 | Cl, Cl, F (phenyl) | 188–189 |
| 6 | Cl, F, Cl (phenyl) | — |

PREPARATION OF THE STARTING COMPOUNDS

Example II-1

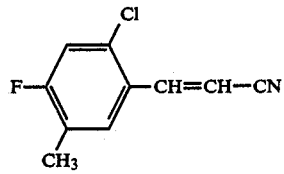

18.2 g (0.12 mol) of diazabicycloundecene in 150 ml tetrahydrofuran are added dropwise, at room temperature and with stirring to 25.1 g (0.11 mol) of 2-chloro-3-(2-chloro-4-fluoro-5-methyl-phenyl)-propionitrile in 100 ml of tetrahydrofuran, when the addition is complete, the mixture is stirred for a further 15 hours at room temperature and filtered, the filtrate is evaporated in vacuo, the residue is taken up in ethyl acetate, the solution is washed with 1-normal hydrochloric acid and water in succession, dried over sodium sulphate, and the solvent is removed in vacuo.

20.2 g (94% of theory) of 3-(2-chloro-4-fluoro-5-methyl-phenyl)-acrylonitrile of melting point 90° C.–91° C. are obtained.

In a corresponding manner and in accordance with the general instructions for the preparation, the following substituted cinnamonitriles of the general formula (II) are obtained:

Ar—CH=CH—CN        (II)

| Example No. | Ar | Physical properties |
|---|---|---|
| II-2 | F, F, Cl (phenyl) | b.p. 83–83° C./ 0.2 mbar |

-continued

| Example No. | Ar | Physical properties |
|---|---|---|
| II-3 | (Cl, F, F on benzene ring) | m.p. 76–77° C. |
| II-4 | (Cl, Cl, F on benzene ring) | m.p. 92–93° C. |

Example IV-1

(a) In a stirring apparatus, 537 g of 2,4-dichloro-trifluoromethoxy-benzene are introduced at 20° C., and 604 g of nitrating acid (33% by weight of nitric acid, 67% by weight of sulphuric acid) are added dropwise. The mixture is then stirred for an hour at 40° C. The nitrating mixture is poured onto ice, the mixture is extracted with dichloromethane, and the organic phase is dried and subjected to precision distillation. In the boiling range 131° to 134° C. at 18 mbar, 551 g of 3-nitro-4,6-dichloro-trifluoromethoxybenzene with a refractive index $n_D^{20}$ of 1.5291 distil over.

(b) In a stirring apparatus, 150 g of potassium fluoride are introduced in 250 ml of tetramethylene sulphone and suspended. 30 ml of the solvent are then distilled off under a vacuum of 18 mbar in order to free the apparatus and the materials employed from water. With the exclusion of humidity, 110 g of 3-nitro-4,6-dichloro-trifluoromethoxy-benzene are then added and stirred for 6 hours at an internal temperature of 190° C. The reaction solution is then cooled to approximately 100° C., and a crude distillation is carried out, in which the product is collected up to a boiling point of 140° C. at 20 mbar. The distillate obtained is washed twice with 100 ml of cold water each time, and is then dried and subjected to precision distillation. 27 g of 3-nitro-4,6-difluoro-trifluoromethoxy-benzene are obtained at a boiling point of 66° to 68° C. at 10 mbar.

(c) In a hydrogenation apparatus, 27 g of 3-nitro-4,6-difluoro-trifluoromethoxy-benzene in 150 ml of tetrahydrofuran are hydrogenated at 30 to 50 bar hydrogen at 25° to 45° C., in the presence of 3 g of Raney nickel. When the hydrogen uptake is complete, the mixture is filtered, and the filtrate is distilled. 19 g of 3-amino-4,6-difluoro-trifluoromethoxy-benzene of a boiling point of 82° to 83° C. at 20 mbar are obtained.

Example IV-b 2

(a) 220 g of nitrating acid (33% by weight of nitric acid, 67% by weight of sulphuric acid) are added dropwise at 50° to 55° C. to 162 g of 2,6-difluoro-benzotrifluoride. The mixture is allowed to react for one hour and poured onto ice, the organic phase is separated off with dichloromethane, dried and distilled. 178 g of 3-nitro-2,6-difluoro-benzotrifluoride of a boiling point of 96° to 100° C. at 22 mbar and a refractive index $n_D^{20}$ of 1.4570 are obtained.

(b) In a hydrogenation apparatus, 178 g of the nitro-compound obtained in (a) in 680 ml of tetrahydrofuran are introduced together with 15 g of Raney nickel, and the mixture is hydrogenated at 30 to 50 bar hydrogen pressure at 25° to 45° C. When the uptake of hydrogen is complete, the mixture is cooled and the pressure is released. The reaction mixture is filtered and distilled, and 147 g of 2,6-difluoro-3-amino-benzotrifluoride of a boiling point of 89° to 90° C. at 18 mbar are obtained.

Example IV-3

In a stainless steel autoclave, 200 ml of tetrahydrofuran and 50 g of 2,4,6-trifluorobenzotrifluoride are introduced, and 30 ml of liquid ammonia are pressed on. The mixture is then heated at 120° C. for 6 hours, with stirring. The reaction mixture is cooled, the pressure is released, and the mixture is subjected to fractional distillation. At a boiling point of 57° to 58° C. at 12 mbar, 15 g of 2-amino-4,6-difluoro-benzotrifluoride are obtained. After a small intermediate cut, 32 g of 2,6-difluoro-4-amino-benzotrifluoride distil over at a boiling point of 103° to 105° C. at 16 mbar. Melting point of the resultant 2,6-difluoro-4-amino-benzotrifluoride: 66° C.

Example IV-4

In a stainless steel autoclave, 500 g of 3,4,5-trifluorobenzotrifluoride are introduced, 2,000 ml of tetrahydrofuran are added, and 150 g of liquid ammonia are forced in. The autoclave is heated to 120° to 130° C. for 5 hours with stirring, then cooled, and the pressure is released at 20° C. In addition to the solvent and the starting material, 272 g of 3,5-difluoro-4-amino-benzotrifluoride of a boiling point of 58° to 60° C. at 16 mbar are obtained by distillation.

Example IV-5

200 g of 2,3,4-trifluorobenzotrifluoride in 500 ml of tetrahydrofuran are introduced in an autoclave, and 60 ml of liquid ammonia are forced in. The mixture is stirred at 130° C. for 6 hours (maximum pressure 18 bar), cooled, and released. By distillation, 72 g of 2-amino-3,4-difluoro-benzotrifluoride are obtained at a boiling point of 60° to 64° C. at 26 mbar and 92 g of 2,3-difluoro-4-amino-benzotrifluoride are obtained at a boiling point of 92° to 93° C. at 26 mbar.

Example V-1

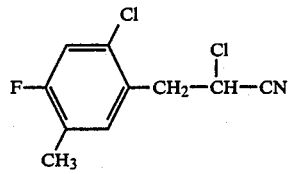

40 ml of 25 per cent hydrochloric acid and 28.8 ml (0.37 mol) of acrylonitrile are added to 19.6 g (0.12 mol) of 2-chloro-4-fluoro-5-methylaniline in 40 ml of acetone, 8.7 g (0.13 mol) of sodium nitrite in 17 ml of water are then added dropwise with stirring at 0° C. to 10° C. in the course of one hour, the mixture is stirred for a further hour at 0° C. to 10° C., and several portions of copper(II) oxide powder are then added, with nitrogen gas vigorously evolving. When the evolution of gas has ended, the mixture is stirred for a further 15 hours at room temperature, dichloromethane is then added, the mixture is washed with water, dried over sodium sulphate and concentrated in vacuo, and the oily residue is purified by chromatography on silica gel (mobile phase: cyclohexane/ethyl acetate 1:1).

25.3 g (90% of theory) of 2-chloro-3-(2-chloro-4-fluoro-5-methylphenyl)-propionitrile are obtained as an oil.

$^1$H-NMR (CDCl$_3$/TMS): $\delta$=2.3 (3 H); 3.4 (2 H); 4.7 (1 H); 7.0–7.2 (2 H) ppm.

In a corresponding manner and in accordance with the general instructions for the preparation, the following α-chloro-β-phenyl-propionitriles of the formula (V) are obtained:

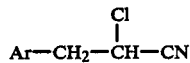

| Example No. | Ar | Physical properties |
|---|---|---|
| V-2 | | $^1$H-NMR*: 3.3; 4.6; 7.3; 7.4 |
| V-3 | | b.p. 75–77° C./ 0.15 mbar |
| V-4 | | b.p. 86–88° C./ 0.1 mbar |

*The $^1$H-NMR spectra were recorded in deuterochloroform (CDCl$_3$) with tetramethylsilane (TMS) as the internal standard. The data indicated represent the chemical shift expressed as δ value in ppm.

Use Example

In the following use example, the compound listed as employed as a comparison substance:

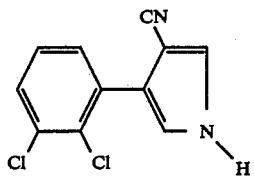

3-cyano-4-(2,3-dichlorophenyl)-pyrrole (cf. EP No. 174,910 and EP No. 236,272).

Example A

Botrytis test (bean)/protective

Solvent 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, the compounds of Preparation Examples 4 and 5, for example, have a considerably superior activity to the prior art.

Example B

Leptosphaeria nodorum-test (wheat)/protective

Solvent; 100 parts by weight dimethylformamide
Emulsifier: 0.25 Parts by weight alkylaryl-polyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidium suspension os Leptosphaeria nodorum. The plants remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, a clearly superior activity compared with the prior art shown, for example, by the compounds according to the preparation examples: 4, 5 and 6.

It is understood that the specification and examples are illustrative but not limitative of the present invention and that other embodiments within the spirit and scope of the invention will suggest themselves to those skilled in the art.

We claim:

1. A 3-cyano-4-pyrrole of the formula

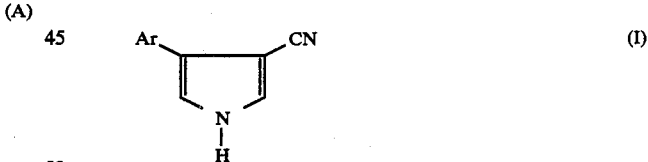

in which
Ar stands for phenyl which is trisubstituted, tetrasubstituted or pentasubstituted by identical or different substituents selected from the group consisting of fluorine, chlorine, bromine, methyl, methoxy, methylthio, trifluoromethyl, trifluoromethoxy, trifluoromethylthio at least one substituent being fluorine.

2. A fungicidal composition comprising a fungicidally effective amount of a compound according to claim 1 and a diluent.

3. A method of combating fungi which comprises applying to such fungi or to a fungus habitat a fungicidally effective amount of a compound according to claim 1.

4. The method according to claim 3, wherein such compound is 3-cyano-4-(4-fluoro-2-chloro-5-methyl-phenyl)-pyrrole, 3-cyano-4-(2,4-difluoro-5-chloro-phenyl)-pyrrole, 3-cyano-4-(2,4-difluoro-3-chloro-phenyl)-pyrrole or 3-cyano-4-(3,4-dichloro-2-fluoro-phenyl)-pyrrole.

5. A compound according to claim 1, wherein such compound is 3-cyano-4-(4-fluoro-2-chloro-5-methyl-phenyl)-pyrrole of the formula

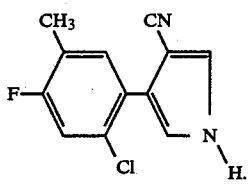

6. A compound according to claim 1, wherein such compound is 3-cyano-4-(2,4-difluoro-5-chloro-phenyl)-pyrrole of the formula

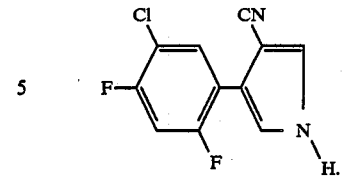

7. A compound according to claim 1, wherein such compound is 3-cyano-4-(3,4-chloro-2-fluoro-phenyl)-pyrrole of the formula

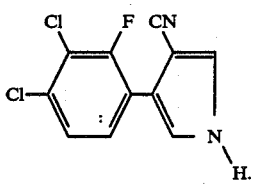

8. A compound according to claim 1, wherein such compound is 3-cyano-4-(2,4-difluoro-3-chloro-phenyl)-pyrrole of the formula

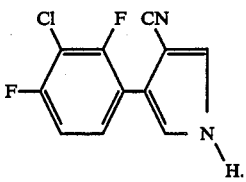

* * * * *

UNITED STATES PATENT AND TRADEMARK OFFICE
CERTIFICATE OF CORRECTION

PATENT NO. : 4,952,601

DATED : August 28, 1990

INVENTOR(S) : Wollweber et al.

It is certified that error appears in the above-identified patent and that said Letters Patent is hereby corrected as shown below:

Col. 20, lines 57-58  After " trifluoromethylthio " insert -- and difluorodioxymethylene --

Col. 22, line 11  Delete " chloro " and substitute -- dichloro --

Signed and Sealed this

Twentieth Day of October, 1992

*Attest:*

DOUGLAS B. COMER

*Attesting Officer*  *Acting Commissioner of Patents and Trademarks*